US011241158B2

(12) United States Patent
Arditi et al.

(10) Patent No.: US 11,241,158 B2
(45) Date of Patent: *Feb. 8, 2022

(54) SYSTEMS, APPARATUSES AND METHODS FOR RADIO FREQUENCY-BASED ATTACHMENT SENSING

(71) Applicant: Zoll Medical Israel Ltd., Kfar-Saba (IL)

(72) Inventors: Gil Arditi, Binyamina (IL); Roman Vaistikh, Ganei Tikva (IL); Uriel Weinstein, Mazkeret Batya (IL)

(73) Assignee: ZOLL MEDICAL ISRAEL LTD., Kfar-Saba (IL)

( * ) Notice: Subject to any disclaimer, the term of this patent is extended or adjusted under 35 U.S.C. 154(b) by 105 days.

This patent is subject to a terminal disclaimer.

(21) Appl. No.: 16/715,919

(22) Filed: Dec. 16, 2019

(65) Prior Publication Data
US 2020/0113447 A1   Apr. 16, 2020

Related U.S. Application Data

(63) Continuation of application No. 14/994,052, filed on Jan. 12, 2016, now Pat. No. 10,548,485.
(Continued)

(51) Int. Cl.
*A61N 1/02* (2006.01)
*A61B 5/0205* (2006.01)
(Continued)

(52) U.S. Cl.
CPC .............. *A61B 5/0205* (2013.01); *A61B 5/05* (2013.01); *A61B 5/318* (2021.01); *A61B 5/0015* (2013.01);
(Continued)

(58) Field of Classification Search
USPC ......................................................... 600/513
See application file for complete search history.

(56) References Cited

U.S. PATENT DOCUMENTS

| 4,240,445 A | 12/1980 | Iskander et al. |
| 4,344,440 A | 8/1982 | Aaby et al. |

(Continued)

FOREIGN PATENT DOCUMENTS

| CN | 101032400 A | 9/2007 |
| CN | 101516437 A | 8/2009 |

(Continued)

OTHER PUBLICATIONS

Alekseev, S. I., et al. "Human Skin permittivity determined by millimeter wave reflection measurements", Bioelectromagnetics, vol. 28, No. 5, Jul. 1, 2007, pp. 331-339.
(Continued)

*Primary Examiner* — Nicole F Lavert
*Assistant Examiner* — Nicole F. Johnson
(74) *Attorney, Agent, or Firm* — Cooley LLP

(57) ABSTRACT

Some embodiments of the present disclosure discuss an apparatus comprising a transceiver configured to generate and/or receive radio frequency (RF) electromagnetic signals, one or more antennae configured to radiate the generated RF electromagnetic signals toward a surface and to output signals corresponding to received reflections of the RF electromagnetic signals, and a processing circuitry configured to process the received reflections and/or the output signals so as to determine change in position of the apparatus with respect to the surface. The apparatus may be incorporated into a wearable garment and/or an adhesive patch, and it may be attached to an outer surface of a human or an animal body.

18 Claims, 4 Drawing Sheets

Related U.S. Application Data

(60) Provisional application No. 62/102,551, filed on Jan. 12, 2015.

(51) Int. Cl.
  A61B 5/05 (2021.01)
  A61B 5/318 (2021.01)
  A61B 5/00 (2006.01)

(52) U.S. Cl.
  CPC .......... *A61B 5/6804* (2013.01); *A61B 5/7235* (2013.01); *A61B 5/746* (2013.01); *A61B 2562/0219* (2013.01); *A61B 2562/166* (2013.01)

(56) References Cited

U.S. PATENT DOCUMENTS

| | | |
|---|---|---|
| 4,557,272 A | 12/1985 | Carr |
| 4,632,128 A | 12/1986 | Paglione et al. |
| 4,640,280 A | 2/1987 | Sterzer |
| 4,641,659 A | 2/1987 | Sepponen |
| 4,774,961 A | 10/1988 | Carr |
| 4,825,880 A | 5/1989 | Stauffer et al. |
| 4,926,868 A | 5/1990 | Larsen |
| 4,945,914 A | 8/1990 | Allen |
| 4,958,638 A | 9/1990 | Sharpe |
| 4,986,870 A | 1/1991 | Frohlich |
| 5,003,622 A | 3/1991 | Ma et al. |
| 5,109,855 A | 5/1992 | Guner |
| 5,394,882 A | 3/1995 | Mawhinney |
| 5,404,877 A | 4/1995 | Nolan |
| 5,474,574 A | 12/1995 | Payne et al. |
| 5,540,727 A | 7/1996 | Tockman et al. |
| 5,549,650 A | 8/1996 | Bornzin et al. |
| 5,668,555 A | 9/1997 | Starr |
| 5,704,355 A | 1/1998 | Bridges |
| 5,766,208 A | 6/1998 | McEwan |
| 5,807,257 A | 9/1998 | Bridges |
| 5,829,437 A | 11/1998 | Bridges |
| 5,841,288 A | 11/1998 | Meaney et al. |
| 5,865,177 A | 2/1999 | Segawa |
| 5,967,986 A | 10/1999 | Cimochowski et al. |
| 6,019,724 A | 2/2000 | Gronningsaeter et al. |
| 6,061,589 A | 5/2000 | Bridges et al. |
| 6,064,903 A | 5/2000 | Riechers et al. |
| 6,093,141 A | 7/2000 | Mosseri et al. |
| 6,144,344 A | 11/2000 | Kim |
| 6,161,036 A | 12/2000 | Matsumara et al. |
| 6,193,669 B1 | 2/2001 | Degany et al. |
| 6,208,286 B1 | 3/2001 | Rostislavovich et al. |
| 6,233,479 B1 | 5/2001 | Haddad et al. |
| 6,267,723 B1 | 7/2001 | Matsumura et al. |
| 6,330,479 B1 | 12/2001 | Stauffer |
| 6,409,662 B1 | 6/2002 | Lloyd et al. |
| 6,454,711 B1 | 9/2002 | Haddad et al. |
| 6,471,655 B1 | 10/2002 | Baura |
| 6,480,733 B1 | 11/2002 | Turcott |
| 6,526,318 B1 | 2/2003 | Ansarinia |
| 6,592,518 B2 | 7/2003 | Denker et al. |
| 6,604,404 B2 | 8/2003 | Paltieli et al. |
| 6,729,336 B2 | 5/2004 | Da Silva et al. |
| 6,730,033 B2 | 5/2004 | Yao et al. |
| 6,755,856 B2 | 6/2004 | Fierens et al. |
| 6,933,811 B2 | 8/2005 | Enokihara et al. |
| 6,940,457 B2 | 9/2005 | Lee et al. |
| 7,020,508 B2 | 3/2006 | Stivoric et al. |
| 7,122,012 B2 | 10/2006 | Bouton et al. |
| 7,130,681 B2 | 10/2006 | Gebhardt et al. |
| 7,184,824 B2 | 2/2007 | Hashimshony |
| 7,191,000 B2 | 3/2007 | Zhu et al. |
| 7,197,356 B2 | 3/2007 | Carr |
| 7,266,407 B2 | 9/2007 | Li et al. |
| 7,267,651 B2 | 9/2007 | Nelson |
| 7,272,431 B2 | 9/2007 | McGrath |
| 7,280,863 B2 | 10/2007 | Shachar |
| 7,454,242 B2 | 11/2008 | Fear et al. |
| 7,474,918 B2 | 1/2009 | Frants et al. |
| 7,479,790 B2 | 1/2009 | Choi |
| 7,493,154 B2 | 2/2009 | Bonner et al. |
| 7,529,398 B2 | 5/2009 | Zwirn et al. |
| 7,570,063 B2 | 8/2009 | Van Veen et al. |
| 7,591,792 B2 | 9/2009 | Bouton |
| 7,697,972 B2 | 4/2010 | Verard et al. |
| 7,719,280 B2 | 5/2010 | Lagae et al. |
| 7,747,302 B2 | 6/2010 | Milledge et al. |
| 7,868,627 B2 | 1/2011 | Turkovskyi |
| 8,032,211 B2 | 10/2011 | Hashimshony et al. |
| 8,211,040 B2 | 7/2012 | Kojima et al. |
| 8,295,920 B2 | 10/2012 | Bouton et al. |
| 8,352,015 B2 | 1/2013 | Bernstein et al. |
| 8,473,054 B2 | 6/2013 | Pillai et al. |
| 8,682,399 B2 | 3/2014 | Rabu |
| 8,882,759 B2 | 11/2014 | Manley et al. |
| 8,938,292 B2 | 1/2015 | Hettrick et al. |
| 8,983,592 B2 | 3/2015 | Belalcazar |
| 8,989,837 B2 | 3/2015 | Weinstein et al. |
| 9,220,420 B2 | 12/2015 | Weinstein et al. |
| 9,265,438 B2 | 2/2016 | Weinstein et al. |
| 9,572,512 B2 | 2/2017 | Weinstein et al. |
| 9,629,561 B2 | 4/2017 | Weinstein et al. |
| 9,788,752 B2 | 10/2017 | Weinstein et al. |
| 10,136,833 B2 | 11/2018 | Weinstein et al. |
| 10,548,485 B2 | 2/2020 | Arditi et al. |
| 10,588,599 B2 | 3/2020 | Weinstein et al. |
| 2002/0032386 A1 | 3/2002 | Sackner et al. |
| 2002/0045836 A1 | 4/2002 | Alkawwas |
| 2002/0049394 A1 | 4/2002 | Roy et al. |
| 2002/0050954 A1 | 5/2002 | Jeong-Kun et al. |
| 2002/0147405 A1 | 10/2002 | Denker et al. |
| 2002/0151816 A1 | 10/2002 | Rich et al. |
| 2003/0036674 A1 | 2/2003 | Bouton |
| 2003/0036713 A1 | 2/2003 | Bouton et al. |
| 2003/0088180 A1 | 5/2003 | Van Veen et al. |
| 2003/0100815 A1 | 5/2003 | Da Silva et al. |
| 2003/0199770 A1 | 10/2003 | Chen et al. |
| 2003/0219598 A1 | 11/2003 | Sakurai |
| 2004/0015087 A1 | 1/2004 | Boric-Lubecke et al. |
| 2004/0073081 A1 | 4/2004 | Schramm |
| 2004/0077943 A1 | 4/2004 | Meaney et al. |
| 2004/0077952 A1 | 4/2004 | Rafter et al. |
| 2004/0249257 A1 | 12/2004 | Tupin et al. |
| 2004/0254457 A1 | 12/2004 | van der Weide |
| 2004/0261721 A1 | 12/2004 | Steger |
| 2005/0038503 A1 | 2/2005 | Greenhalgh et al. |
| 2005/0107693 A1 | 5/2005 | Fear et al. |
| 2005/0192488 A1 | 9/2005 | Bryenton |
| 2005/0245816 A1 | 11/2005 | Candidus et al. |
| 2006/0004269 A9 | 1/2006 | Caduff et al. |
| 2006/0009813 A1 | 1/2006 | Taylor et al. |
| 2006/0025661 A1 | 2/2006 | Sweeney et al. |
| 2006/0101917 A1 | 5/2006 | Merkel |
| 2006/0237223 A1 | 10/2006 | Chen et al. |
| 2006/0265034 A1 | 11/2006 | Aknine et al. |
| 2007/0016032 A1 | 1/2007 | Aknine |
| 2007/0016050 A1 | 1/2007 | Moehring et al. |
| 2007/0055123 A1 | 3/2007 | Takiguchi |
| 2007/0100385 A1 | 5/2007 | Prashant |
| 2007/0123770 A1 | 5/2007 | Bouton et al. |
| 2007/0123778 A1 | 5/2007 | Kantorovich |
| 2007/0135721 A1 | 6/2007 | Zdeblick |
| 2007/0152812 A1 | 7/2007 | Wong et al. |
| 2007/0156057 A1 | 7/2007 | Cho et al. |
| 2007/0162090 A1 | 7/2007 | Penner |
| 2007/0191733 A1 | 8/2007 | Gianchandani et al. |
| 2007/0263907 A1 | 11/2007 | McMakin et al. |
| 2008/0027313 A1 | 1/2008 | Shachar |
| 2008/0030284 A1 | 2/2008 | Tanaka et al. |
| 2008/0036668 A1 | 2/2008 | White et al. |
| 2008/0097199 A1 | 4/2008 | Mullen |
| 2008/0129511 A1 | 6/2008 | Yuen et al. |
| 2008/0139934 A1 | 6/2008 | McMorrow et al. |
| 2008/0167566 A1 | 7/2008 | Kamil et al. |
| 2008/0169961 A1 | 7/2008 | Steinway et al. |

(56) References Cited

U.S. PATENT DOCUMENTS

| | | |
|---|---|---|
| 2008/0183247 A1 | 7/2008 | Harding |
| 2008/0200802 A1 | 8/2008 | Bahavaraju et al. |
| 2008/0224688 A1 | 9/2008 | Rubinsky et al. |
| 2008/0269589 A1 | 10/2008 | Thijs et al. |
| 2008/0283282 A1 | 11/2008 | Kawasaki et al. |
| 2008/0294036 A1 | 11/2008 | Hoi et al. |
| 2008/0316124 A1 | 12/2008 | Hook |
| 2008/0319301 A1 | 12/2008 | Busse |
| 2009/0021720 A1 | 1/2009 | Hecker |
| 2009/0048500 A1 | 2/2009 | Corn |
| 2009/0076350 A1 | 3/2009 | Bly et al. |
| 2009/0153412 A1 | 6/2009 | Chiang et al. |
| 2009/0153433 A1 | 6/2009 | Nagai et al. |
| 2009/0187109 A1 | 7/2009 | Hashimshony |
| 2009/0203972 A1 | 8/2009 | Heneghan et al. |
| 2009/0227882 A1 | 9/2009 | Foo |
| 2009/0240132 A1 | 9/2009 | Friedman |
| 2009/0240133 A1 | 9/2009 | Friedman |
| 2009/0248450 A1 | 10/2009 | Fernandez |
| 2009/0262028 A1 | 10/2009 | Mumbru et al. |
| 2009/0281412 A1 | 11/2009 | Boyden et al. |
| 2009/0299175 A1 | 12/2009 | Bernstein et al. |
| 2009/0312615 A1 | 12/2009 | Caduff et al. |
| 2009/0322636 A1 | 12/2009 | Brigham et al. |
| 2010/0004517 A1 | 1/2010 | Bryenton |
| 2010/0013318 A1 | 1/2010 | Iguchi et al. |
| 2010/0052992 A1 | 3/2010 | Okamura et al. |
| 2010/0056907 A1 | 3/2010 | Rappaport et al. |
| 2010/0076315 A1 | 3/2010 | Erkamp et al. |
| 2010/0081895 A1 | 4/2010 | Zand |
| 2010/0106223 A1 | 4/2010 | Grevious |
| 2010/0152600 A1 | 6/2010 | Droitcour et al. |
| 2010/0256462 A1 | 10/2010 | Rappaport et al. |
| 2010/0265159 A1 | 10/2010 | Ando et al. |
| 2010/0305460 A1 | 12/2010 | Pinter et al. |
| 2010/0312301 A1 | 12/2010 | Stahmann |
| 2010/0321253 A1 | 12/2010 | Vazquez et al. |
| 2010/0332173 A1 | 12/2010 | Watson et al. |
| 2011/0004076 A1 | 1/2011 | Janna et al. |
| 2011/0009754 A1 | 1/2011 | Wenzel et al. |
| 2011/0022325 A1 | 1/2011 | Craddock et al. |
| 2011/0040176 A1 | 2/2011 | Razansky et al. |
| 2011/0060215 A1 | 3/2011 | Tupin et al. |
| 2011/0068995 A1 | 3/2011 | Baliarda et al. |
| 2011/0125207 A1 | 5/2011 | Nabutovsky et al. |
| 2011/0130800 A1* | 6/2011 | Weinstein ............ A61B 8/4254 607/17 |
| 2011/0257555 A1 | 10/2011 | Banet et al. |
| 2012/0029323 A1 | 2/2012 | Zhao |
| 2012/0065514 A1 | 3/2012 | Naghavi et al. |
| 2012/0068906 A1 | 3/2012 | Asher et al. |
| 2012/0098706 A1 | 4/2012 | Lin et al. |
| 2012/0104103 A1 | 5/2012 | Manzi |
| 2012/0330151 A1 | 12/2012 | Weinstein et al. |
| 2013/0041268 A1 | 2/2013 | Rimoldi et al. |
| 2013/0053671 A1 | 2/2013 | Farra |
| 2013/0069780 A1 | 3/2013 | Tran et al. |
| 2013/0090566 A1 | 4/2013 | Muhlsteff et al. |
| 2013/0123614 A1 | 5/2013 | Bernstein et al. |
| 2013/0184573 A1 | 7/2013 | Pahlevan et al. |
| 2013/0190646 A1 | 7/2013 | Weinstein et al. |
| 2013/0225989 A1 | 8/2013 | Saroka et al. |
| 2013/0231550 A1 | 9/2013 | Weinstein et al. |
| 2013/0297344 A1 | 11/2013 | Cosentino et al. |
| 2013/0310700 A1 | 11/2013 | Wiard et al. |
| 2014/0046690 A1 | 2/2014 | Gunderson et al. |
| 2014/0081159 A1 | 3/2014 | Tao et al. |
| 2014/0128032 A1* | 5/2014 | Muthukumar ........ H04W 4/12 455/411 |
| 2014/0163425 A1 | 6/2014 | Tran |
| 2014/0288436 A1 | 9/2014 | Venkatraman et al. |
| 2015/0025333 A1 | 1/2015 | Weinstein et al. |
| 2015/0150477 A1 | 6/2015 | Weinstein et al. |
| 2015/0164349 A1 | 6/2015 | Gopalakrishnan et al. |
| 2015/0335310 A1 | 11/2015 | Bernstein et al. |
| 2016/0073924 A1 | 3/2016 | Weinstein et al. |
| 2016/0198957 A1 | 7/2016 | Arditi et al. |
| 2016/0198976 A1 | 7/2016 | Weinstein et al. |
| 2016/0213321 A1 | 7/2016 | Weinstein et al. |
| 2016/0317054 A1 | 11/2016 | Weinstein et al. |
| 2016/0345845 A1 | 12/2016 | Ravid et al. |
| 2017/0035327 A1 | 2/2017 | Yuen et al. |
| 2017/0135598 A1 | 5/2017 | Weinstein et al. |
| 2017/0238966 A1 | 8/2017 | Weinstein et al. |
| 2017/0296093 A1 | 10/2017 | Weinstein et al. |
| 2019/0046038 A1 | 2/2019 | Weinstein et al. |
| 2019/0298208 A1 | 10/2019 | Weinstein et al. |

FOREIGN PATENT DOCUMENTS

| | | |
|---|---|---|
| DE | 10008886 | 9/2001 |
| EP | 1834588 A1 | 9/2007 |
| EP | 2506917 A1 | 10/2012 |
| EP | 2 602 870 A1 | 6/2013 |
| JP | 05-038957 | 5/1993 |
| JP | 10-137193 A | 5/1998 |
| JP | 2000-235006 A | 8/2000 |
| JP | 2001-525925 A | 12/2001 |
| JP | 2002-094321 | 3/2002 |
| JP | 2003-141466 | 5/2003 |
| JP | 2004-526488 A | 9/2004 |
| JP | 2006-208070 A | 8/2006 |
| JP | 2006-319767 A | 11/2006 |
| JP | 2007-061359 A | 3/2007 |
| JP | 2007-149959 | 6/2007 |
| JP | 2008-515548 A | 5/2008 |
| JP | 2008-148141 A | 6/2008 |
| JP | 2008-518706 A | 6/2008 |
| JP | 2008-530546 A | 7/2008 |
| JP | 2008-542759 A | 11/2008 |
| JP | 2008-545471 | 12/2008 |
| JP | 2009-514619 A | 4/2009 |
| JP | 2009-522034 A | 6/2009 |
| JP | 2010-507929 | 3/2010 |
| JP | 2010-072957 | 4/2010 |
| JP | 2010-512190 A | 4/2010 |
| JP | 2010-530769 | 9/2010 |
| JP | 2010-537766 A | 12/2010 |
| JP | 2011-507583 A | 3/2011 |
| JP | 2011-524213 A | 9/2011 |
| JP | 2012-090257 | 5/2012 |
| WO | WO 02/03499 A1 | 1/2002 |
| WO | WO 2003/009752 A2 | 2/2003 |
| WO | WO 2006/127719 A2 | 11/2006 |
| WO | WO 2006/130798 A2 | 12/2006 |
| WO | WO 2007/017861 A2 | 2/2007 |
| WO | WO 2007/023426 A2 | 3/2007 |
| WO | WO 2008/070856 A2 | 6/2008 |
| WO | WO 2008/148040 A1 | 12/2008 |
| WO | WO 2009/031149 A2 | 3/2009 |
| WO | WO 2009/031150 A2 | 3/2009 |
| WO | WO 2009/060182 A1 | 5/2009 |
| WO | WO 2009/081331 A1 | 7/2009 |
| WO | WO 2009/152625 A1 | 12/2009 |
| WO | WO 2011/067623 A1 | 6/2011 |
| WO | WO 2011/067685 A1 | 6/2011 |
| WO | WO 2011/141915 A2 | 11/2011 |
| WO | WO 2012/011065 A1 | 1/2012 |
| WO | WO 2012/011066 A1 | 1/2012 |
| WO | WO 2013/118121 A1 | 8/2013 |
| WO | WO 2013/121290 A2 | 8/2013 |
| WO | WO 2015/118544 A1 | 8/2015 |

OTHER PUBLICATIONS

Ascension Technology Corporation, "TrakSTAR Adds Versatility to Ascension's New Product Line: Desktop Model Joins driveBAY Tracker for Fast Guidance of Miniaturized Sensor", USA, Apr. 7, 2008.

Bell et al., "A Low-Profile Achimedean Spiral Antenna Using an EBG Ground Plane", IEEE Antennas and Wireless Propagation Letters 3, pp. 223-226 (2004).

(56) References Cited

OTHER PUBLICATIONS

Beyer-Enke et al., Intra-arterial Doppler flowmetry in the superficial femoral artery following angioplasty., 2000, European Radiology, vol. 10, No. 4, p. 642-649.
Claron Technology Inc., "MicronTracker 3:A New Generation of Optical Trackers", Canada, 2009.
Czum et al., "The Vascular Diagnostic Laboratory", The Heart & Vascular Institute Newsletter, vol. 1, USA, Winter, 2001.
Extended Search Report for European Application No. 11809360.8, dated Mar. 11, 2014.
Ghosh, et al., Immediate Evaluation of Angioplasty and Stenting Results in Supra-Aortic Arteries by Use of a Doppler-Tipped Guidewire, Aug. 2004, American Journal of Neuroradiology, vol. 25, p. 1172-1176.
Gentili et al., "A Versatile Microwave Plethysmograph for the Monitoring of Physiological Parameters", IEEE Transactions on Biomedical Engineering, IEEE Service Center, Pitscataway, NJ, US, vol. 49, No. 10, Oct. 1, 2002.
Haude et al., Intracoronary Doppler-and Quantitative Coronary Angiography-Derived Predictors of Major Adverse Cardiac Events After Stent Implantation, Mar. 6, 2001, Circulation, vol. 103(9), p. 1212-1217.
Immersion Corporation, "Immersion Introduces New 3D Digitizing Product-MicroScribe G2; Faster Data Transfer, USB Compatibility, New Industrial Design", Press Release, San Jose, USA, Jul. 1, 2002.
International Preliminary Report on Patentability, dated Jan. 31, 2013, for International Application No. PCT/IB2011/053246, 22 pages.
International Preliminary Report on Patentability, dated Aug. 19, 2014 for International Application No. PCT/IB2013/000663 filed Feb. 15, 2013.
International Preliminary Report on Patentability, dated Jun. 5, 2012, for International Application No. PCT/IB2010/054861.
Kantarci et al., Follow-Up of Extracranial Vertebral Artery Stents with Doppler Sonography., Sep. 2006, American Journal of Roentgenology, vol. 187, p. 779-787.
Lal et al., "Duplex ultrasound velocity criteria for the stented carotid artery", Journal of Vascular Surgery, vol. 47, No. 1, pp. 63-73, Jan. 2008.
Larsson et al., "State Diagrams of the Heart—a New Approach to Describing Cardiac Mechanics", Cardiovascular Ultrasound 7:22 (2009).
Liang, Jing et al., Microstrip Patch Antennas on Tunable Electromagnetic Band-Gap Substrates, IEEE Transactions on Antennas and Propagation, vol. 57, No. 6, Jun. 2009.
Lin, J.C. et al., "Microwave Imaging of Cerebral Edema", Proceedings of the IEEE, IEEE, NY, US, vol. 70, No. 5; May 1, 1982, pp. 523-524.
Lin et al: "Using dual-antenna nanosecond pulse near field sensing technology for non-contact and continuous blood pressure measurement", Engineering in Medicine and Biology Society (EMBC), 2013 35th Annual International Conference of the IEEE, IEEE, Aug. 28, 2012 (Aug. 28, 2012), pp. 219-222.
Miura et al. "Time Domain Reflectometry: Measurement of Free Water in Normal Lung and Pulmonary Edema," American Journal of Physiology—Lung Physiology 276:1 (1999), pp. L207-L212.
Paulson, Christine N., et al. "Ultra-wideband radar methods and techniques of medical sensing and imaging" Proceedings of Spie, vol. 6007, Nov. 9, 2005, p. 60070L.
Pedersen, P.C., et al., "Microwave Reflection and Transmission Measurements for Pulmonary Diagnosis and Monitoring", IEEE Transactions on Biomedical Engineering, IEEE Service Center, Piscataway, NJ, US, vol. BME-19, No. 1, Jan. 1, 1978; pp. 40-48.
Polhemus, "Fastrak: The Fast and Easy Digital Tracker", USA, 2008.
Ringer et al., Follow-up of Stented Carotid Arteries by Doppler Ultrasound, Sep. 2002, Neurosurgery, vol. 51, No. 3, p. 639-643.
Solberg et al: "A feasibility study on aortic pressure estimation using UWB radar", Ultra-Wideband, 2009. ICUWB 2009. IEEE International Conference On, IEEE, Piscataway, NJ, USA, Sep. 9, 2009 (Sep. 9, 2009), pp. 464-468.
Yang, F. et al. "Enhancement of Printed Dipole Antennas Characteristics Using Semi-EBG Ground Plane", Journal of Electromagnetic Waves and Application, U.S., Taylor & Francis, Apr. 3, 2006, vol. 8, pp. 993-1006.

\* cited by examiner

SYSTEMS, APPARATUSES AND METHODS FOR RADIO FREQUENCY-BASED ATTACHMENT SENSING

CROSS REFERENCES TO RELATED APPLICATIONS

This application is a continuation of U.S. patent application Ser. No. 14/994,052, filed Jan. 12, 2016, entitled "System, Apparatuses and Methods for Radio Frequency-Based Attachment Sensing", issued as U.S. Pat. No. 10,548,485 on Apr. 16, 2020, which claims benefit of and priority to U.S. Provisional Patent Application No. 62/102,551, entitled, "Systems, Apparatuses and Methods for Radio Frequency-based Attachment Sensing," filed Jan. 12, 2015, the disclosure of which is herein incorporated by reference in its entirety.

BACKGROUND

Radio-frequency (RF) electromagnetic radiation has been used for diagnosis and imaging of body tissues, examples of which may be found in PCT Patent Publication No. WO2011/067623, US Patent Publication Nos. 2009/0299175 and 2009/0240133, and U.S. Pat. Nos. 4,926,868, 5,766,208 and 6,061,589. Each of those disclosures is herein incorporated by reference in its entirety.

SUMMARY OF SOME OF THE EMBODIMENTS

Embodiments of antenna implementations discuss an apparatus comprising a transceiver configured to generate and/or receive radio frequency (RF) electromagnetic signals; one or more antennae configured to radiate the generated RF electromagnetic signals toward a surface and to output signals corresponding to received reflections of the RF electromagnetic signals; and a processing circuitry configured to process the received reflections and/or the output signals so as to determine change in position of the apparatus with respect to the surface. The apparatus may be incorporated into a wearable garment and/or an adhesive patch, and/or attached to an outer surface of a human body or an animal body. In some embodiments, the received RF electromagnetic signals may be reflected from the outer surface of a human or an animal body.

In some instances, the RF electromagnetic signals range in frequency from about 300 MHz to about 3 GHz. In some instances, the signals may range in frequency from about 300 MHz to about 300 GHz. In some instances, the received RF electromagnetic signals may be reflected from the surface.

In some embodiments, the one or more antennae may comprise a monostatic antenna element, a bistatic antenna element, and/or a polystatic antenna element. Further, the one or more antennae may comprise a flexible plane configured to conform to the surface, wherein the flexible plane comprises a printed circuit board.

In some embodiments, the apparatus further comprises an electrode configured to measure electrocardiographic signals of the human body or the animal body so as to determine attachment level of the apparatus to the human body or the animal body. It may also comprise a wireless communication unit or module configured to wirelessly communicate with an external module. In some instances, it may further contain an alarm unit configured to provide a warning when the determination of the change in position of the apparatus with respect to the surface indicates attachment of the apparatus to the surface is below a predetermined attachment level threshold.

In some embodiments, the apparatus is configured to detect surface movements that are indicative of physiological effects, examples of which include heartbeat, muscle movement, and respiration. In some instances, the apparatus may be connected to a device for measuring physiological parameters, and may further comprise a switch unit configured to activate or deactivate the device based on the determination of the change in position of the apparatus with respect to the surface. In such implementations, the determination of the change in position of the apparatus with respect to the surface may indicate attachment of the apparatus to the surface is below a predetermined attachment level threshold. In some embodiments, the processing of the generated and/or the received signals comprises analyzing amplitudes and/or phases of the generated and/or the received signals. For example, the analysis of the amplitudes and/or the phases of the generated and/or the received signals comprises comparing changes in amplitudes and/or phases between the generated and the received signals to respective changes in amplitudes and/or phases recorded when the apparatus is at rest with respect to the surface. In some embodiments, such analysis may include determining signal delays of the generated and/or the received signals.

In some embodiments, a method for sensing change in position of an apparatus with respect to a surface to which the apparatus is secured to is disclosed. Such a method may comprise the step of generating and receiving, by a transceiver, radio frequency (RF) electromagnetic signals. It may also include radiating, by one or more antennae, the generated RF electromagnetic signals into the surface the apparatus is secured to; and outputting signals by the one or more antennae and in response to received reflected RF electromagnetic signals. In addition, it may comprise processing the received and/or the output signals so as to determine change in position of the apparatus with respect to the surface.

In some embodiments, a method for sensing attachment level of an apparatus with respect to a body surface to which the apparatus is attached to is disclosed. The method comprises generating and receiving, by a transceiver, radio frequency (RF) electromagnetic signals; and radiating, by one or more antennae, RF electromagnetic signals generated by a transceiver onto the body surface the apparatus is attached to. In some instances, the method includes outputting signals by the one or more antennae in response to RF electromagnetic signals reflected by the body surface; and analyzing the output signals with respect to a nominal signal to determine a shift in the attachment of the apparatus to the body surface, wherein the nominal signal is detected when the apparatus is securely attached to the body surface. For example, analyzing the output signals with respect to the nominal signal comprises calculating sum of absolute values of differences of amplitudes of the reflected signal from amplitudes of the nominal signal per frequency.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION OF SOME OF THE EMBODIMENTS

Figure 1:
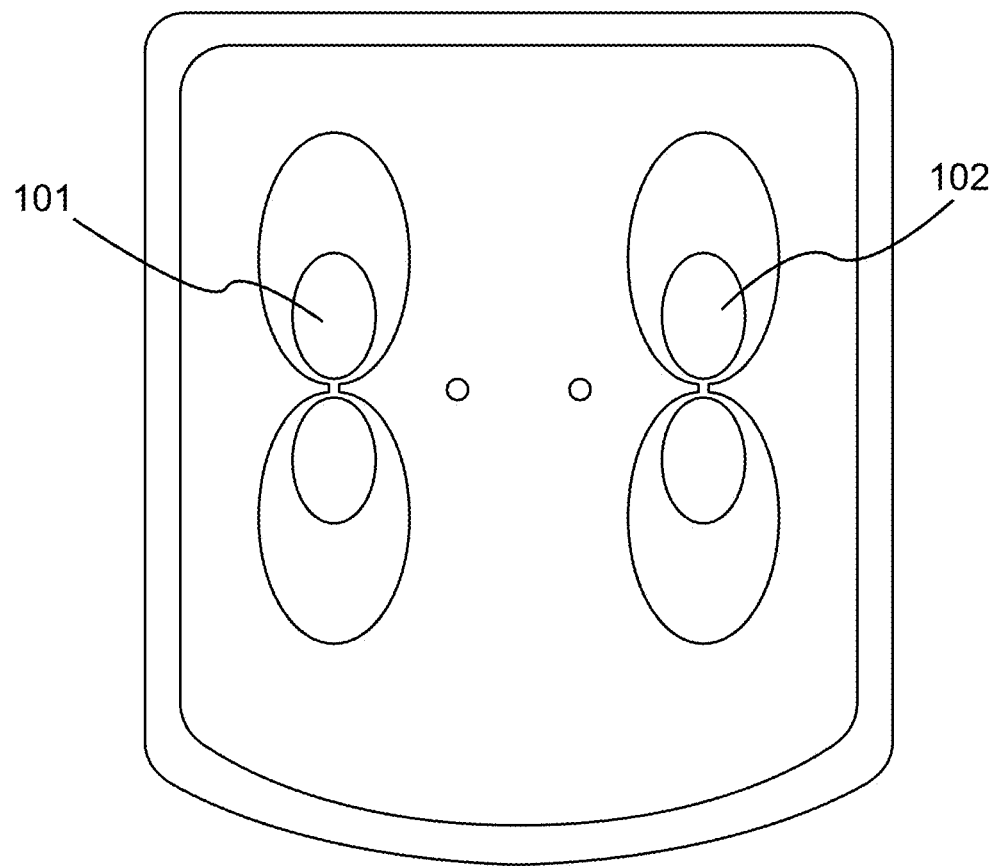
FIG. 1 shows a picture of an example bistatic antenna for sensing attachment to a surface.

In some embodiments of the present disclosure, systems and apparatuses for radio frequency (RF)-based surface attachment sensing are presented. For example, in some embodiments, a sensing apparatus for sensing change in position of the apparatus with respect to a surface comprises one or more antennae, a transceiver, and a processing circuitry. In some embodiments, the sensing apparatus may comprise one or more antennae and a transceiver, and the apparatus may be operationally coupled to the processing circuitry. In some instances, the apparatus may be in direct contact with the surface (with or without adhesives, for example), and sensing and/or measuring the shift of the apparatus with respect to the surface may indicate the attachment level of the apparatus to the surface. In some instances, the apparatus may not be in direct contact to the surface but secured or stably connected to it. For example, the apparatus, while not directly contacting the surface, may be incorporated into a garment or patch that is secured to the surface. In some embodiments, the surface may be an outer surface of a human or an animal body, such as the skin.

In some embodiments, the transceiver can generate driving signals for transmission by the one or more antenna, and may further filter and interpret reflected and propagated signals that are received by the antennae. The transceiver may generate the signals at multiple different frequencies, and when signals are received by the antennae, the received signals may be digitized by the transceiver. In some instances, some or all of the signals may be reflected by the surface and/or body tissues along the path of the signals. For example, RF signals generated by a transceiver and radiated by an antenna of an apparatus attached to the surface of a human or animal body may be reflected by the skin, scattered by body tissues along the propagation path, and/or emerge on substantially opposite side of the body as propagated waves. In some instances, the apparatus may comprise additional antennae on the opposite side of the body to receive the propagated waves.

In some embodiments, the antenna comprises a single antenna element (monostatic antenna), a bistatic antennae (two antenna elements), and/or polystatic or multistatic antennae (more than two antennae elements). In a monostatic mode, the antenna may switch between transmitting and receiving modes, and radiate RF signals and receive reflected waves back from the surface the apparatus is attached to, and/or other tissues on the path of the radiated wave. In bistatic and polystatic modes, antenna elements may comprise a plurality of antenna elements, each tasked with transmitting or receiving RF signals. For example, a bistatic antenna may have one antenna element radiating RF signals and another element receiving waves that are reflected as well as waves radiated by other antenna elements. In some embodiments, the RF signals waveform can be continuous or based on step frequency, and may be radiated in the frequency range of from about 200 MHz to about 300 GHz. The RF signals may also be radiated in the frequency range from about 250 MHz to about 100 GHz, from about 300 MHz to about 30 GHz, from about 300 MHz to about 3 GHz, from about 500 MHz to about 1 GHz, about 300 MHz, about 3 GHz, and/or the like. In yet some instances, higher and lower frequencies outside these ranges may be used. In some of these embodiments, the various frequency elements may be used to improve the performance of the apparatus. For example, multiple frequencies (e.g., from any of the above-noted frequency ranges) may be used to improve detection. Modulation of the frequencies may allow reduction or elimination of interferences. The RF signals may also be configured so as to achieve a range (e.g., depth) resolution that allows effective filtering of reflections from different depths of the surface of the body.

Various types of antennas may be used in implementing embodiments of the present disclosure, including wire antennas (e.g., monopole, dipole, loop antennas, etc.), microstrip antennas (e.g., patch, planar), aperture antennas (e.g., slot, cavity-backed, planar), traveling wave antennas (e.g., helical), printed antennas and/or the like. For example, planar antenna backed by an in-phase reflective structure based on an electromagnetic band gap (EBG) structure between an antenna ground plane and the front surface may be used. Such structures are especially advantageous for providing flat, and possibly flexible antenna, that may conform to a body surface. In some instances, the antennae may comprise a flexible plane attached to said surface. For example, the antenna may be printed on a flexible printed circuit board (PCB). In some instances, planar antenna comprising a conductive element (e.g., spiral) on the front surface of the antenna may be used. Conductive elements in such antennae may be able to receive electrocardiogram (ECG) signals from the body surface, obviating the need for separate ECG electrodes. In some instances, the conductive elements may be included in printed circuit boards that the antennae comprise on the front surface of the antenna.

In some embodiments, the apparatus may comprise a processing circuitry that includes a processor capable of processing signals received by the one or more antennae and/or the transceiver to determine attachment level of the apparatus to the surface the signals are reflected from or propagated through. In some embodiments, the apparatus may not comprise the processing circuitry, but instead may be operationally coupled to the circuitry. In some instances, the processor accomplishes this task by analyzing the amplitudes and/or phases of these signals. For example, the sensing apparatus may process the reflected signals to determine the change in the amplitude and/or phase of the reflected/propagated signals with respect to the signals that were radiated into the surface by the antennae. The processor may then compare these changes to benchmark changes to determine the attachment level of the apparatus to the surface. Examples of benchmark changes are changes in amplitudes and/or phases that have been previously recorded under known conditions. For example, a measurement for amplitude and/or phase changes may be made when the attachment level of the apparatus to the surface is known (e.g., the apparatus is not moving with respect to the surface, the apparatus is directly attached to the surface, the apparatus is in proximity to the surface within a known separation distance, the apparatus is incorporated into a wearable garment or adhesive patch, etc.). Such measurements may then be used as benchmarks for comparison with amplitude/ phase changes that the processer determines by analyzing the reflected and/or propagated signals. In some embodiments, the sensing apparatus may process the reflected signals to determine signal delays of the generated and/or the reflected signals. For example, the signal delays may be obtained from an analysis of the phases of the signals.

In some embodiments, the apparatus may process the reflected signals to determine the change in the amplitude and/or phase of the reflected/propagated signals with respect to a nominal signal when the attachment level of the sensing apparatus to the surface is known (e.g., the nominal signal corresponds to when the apparatus is not moving with respect to the surface, the apparatus is directly attached to the surface, the apparatus is in proximity to the surface within a known separation distance, the apparatus is incorporated into a wearable garment or adhesive patch, etc.). The changes may then be used as measures of attachment levels. For example, a measure of attachment can be determined, in some embodiments, according to the following procedure. First, a nominal signal (including the amplitude thereof) is detected upon the apparatus being attached to a surface of a body (e.g., skin). RF signals are then transmitted from antenna and, reflections therefrom are received by the antenna (either the same antenna or another antenna). The reflected signals are then analyzed to determine the amplitudes of reflected signals with respect to the amplitudes of the nominal signal, for example, by calculating the sum of the absolute value of the difference of the reflected signal amplitude per frequency from a nominal amplitude set. The difference may represent the state of attachment.

In some embodiments, one may wish to check that the sensing apparatus has not been removed from the intended subject (usually a living being such as a human or animal), either intentionally or accidentally, so as to protect the integrity of the measurement results. For example, the apparatus may be attached to a non-living stationary surface and indicate undisturbed attachment, leading to misleading interpretations. In such situations, one may utilize an accelerometer to better determine if the subject the apparatus is intended to be attached to is in fact a living being or not, or at least capable of movement. For example, an accelerometer can be used to better distinguish between attachment to a stationary surface and attachment to living being or tissue (that is, a body capable of movement). In some embodiments, this can be performed by calculating the amount of accelerometer signal energy in low frequencies compared to the energy of the entire spectrum.

In some embodiments, the processing circuitry comprises a combination of dedicated hardware circuits and programmable components. Programmable processors, such as a general-purpose microprocessor, a digital signal processor, etc., which are programmed in software may be used to carry out the tasks described herein. In some implementations, the processing circuitry may comprise dedicated or programmable digital logic units such as an application-specific integrated circuit (ASIC) or a field-programmable gate array (FPGA). In some instances, the tasks may be carried out by a single processor, or by a combination of one or more processors.

In some embodiments, the processing unit may communicate with an external server or device via a communication unit or module that may or may not be a component of the sensing apparatus. For example, any of the measurements obtained and/or processed by the processing unit may be transmitted to an external device by the communication unit. In addition, the communication unit may be configured to receive any data, instructions, etc., from an external device.

The apparatus as described herein may be utilized for a variety of purposes, an example of which is to determine if devices used for measuring physiological parameters on a human or animal skin have maintained their contact with the skin. For example, devices or sensors such as an ECG sensor, photoplethysmogram (PPG) sensor, etc., may be securely attached to the sensing apparatus described herein, and the apparatus/sensor may be used to check on the attachment level of the apparatus itself (and hence the ECG, PPG devices) to the skin as the devices are taking measurements. In some embodiments, the apparatus may comprise an electrode or a conductive element that is configured to receive ECG, PPG, etc., signals from the surface the apparatus is attached to. In such embodiments, the apparatus itself may also serve as a physiological sensor (e.g., ECG and/or PPG devices). In such embodiments, the apparatus may use the measurements of a body as proxy measures of attachment levels of the apparatus to the surface of the body. For example, the processor of the processing unit contained by or operationally coupled to the apparatus may process the measured signals to compare those to benchmark or expected activities of the body. Deviations from the benchmark or expected activities may indicate that the attachment level of the apparatus is different from the attachment level when the benchmark or expected activities were observed. For example, a decreased intensity in the measured ECG or PPG activities may be interpreted as: the apparatus not being securely attached to the surface, the apparatus not being directly attached to the surface, the apparatus moving with respect to the surface, etc. In some embodiments, the apparatus may detect surface movements that are indicative of physiological effects, and these measurements may be used for, for example, diagnostic values. For example, the apparatus may detect minute movements of the surface the apparatus or the antennae are attached to (e.g., blood vessel, muscle, skin movements such as contractions and relaxations), and from the measurements, one may make diagnostic determinations about heartbeat, muscle movement, respiration, etc. Examples of muscle movements include movements of muscles of mastication, movements of muscles of swallowing, and/or the like.

In some embodiments, the devices may not necessarily be configured to receive signals from the body or tissue. For example, the devices may comprise electrodes that provide energy or current to the body such as, but not limited to, defibrillators that provide electrical current into the body. The electrodes may be configured to be attached to the outer surface of a human or an animal body, and the electrode may provide electrical current to the body.

In using the apparatus to measure attachment levels or even ECG/PPG activities, in some embodiments, it may be of interest to determine that the body of the surface to which the apparatus is attached to is a living body/tissue. For example, the attachment level measurements from the apparatus may indicate that the apparatus is firmly attached to the surface. However, the surface may not in fact be the surface of the body for which the attachment measurements are desired. For example, the surface may be some still surface that in fact may not be, for example, the skin of the body whose physiological parameters are being measured the apparatus or a sensor attached thereto (e.g., the sensor falls off a skin and attaches to a still surface, and upon measurement, this may lead to the inaccurate conclusion that the sensor is attached well to the skin). In some embodiments, the apparatus may comprise an accelerometer that detects movements of the apparatus, and by extension, devices and bodies securely attached to the apparatus. In some embodiments, the apparatus may comprise, or be incorporated into, other sensors/detectors such as but not limited to lie detectors, photoplethysmogram (PPG) sensors, ECG sensors, etc. In addition, the apparatus may be utilized to verify the efficacy of other surface attachment systems. For example, the apparatus can be incorporated into the surface attachment system of an insulin pump attachment so as to monitor and verify the effectiveness of the attachment system to the body to which the insulin pump is attached. Similarly, the apparatus can be incorporated into other attachment systems used to attach the aforementioned sensors (PPG sensors, ECG sensors, accelerometers, defibrillators, etc.) to a body. Further, the disclosed apparatus may be used with seatbelts where the apparatus may be used to verify and/or monitor whether seatbelts are properly in contact with users of the seatbelts. In some instances, this may provide additional information on the state of the body the apparatus is attached to (e.g., if the accelerometer indicates no movement on the part of the body for an extended period of time, then this may be an indication that the attachment may not have been to a living body or tissue).

In some embodiments, the apparatus disclosed herein may also be used to determine the locations of subcutaneous devices, examples of which include implants, subcutaneous devices, guiding sensors (e.g., guidance sensors used for subcutaneous needles, etc.). In some embodiments, the disclosed RF-based surface attachment sensing apparatus may direct RF signals towards locations of subcutaneous devices in a body, and based on an analysis of the reflection signals or patterns may determine the locations and/or change in locations of the devices. For example, changes in the amplitude phases, and/or signal delays of the reflected signals may be compared to benchmark values for indications on the locations and/or shifts in locations of the subcutaneous devices. In some embodiments, the verification or monitoring of the subcutaneous devices may be performed in real time, providing valuable feedback to a user of the disclosed apparatus (e.g., surgeon using a subcutaneous needle may use the disclosed apparatus to track the progress of the needle inside a patient's body).

In some embodiments, the apparatus or a sensor associated (e.g., securely connected) with the apparatus may be performing a physiological measurement of a body, and the apparatus may indicate that the attachment level of the apparatus/sensor is different from the appropriate level of attachment for performing the measurement. For example, the apparatus may comprise an alarm component that provides a warning when the attachment is below a predetermined attachment level threshold. The warning may be visual (e.g., lights, textual displays, etc.), auditory (e.g., a warning via a speaker contained in the apparatus), tactile, and/or the like. In some instances, the apparatus may provide a value indicating the attachment level. For example, from analyzing the reflected and/or the propagated signals and/or measurements of ECG activities, the sensor may determine and assign a value to the attachment level (e.g., a 10% reduction in the intensity of ECG activities translates to an 85% attachment level based on a pre-determined calibration scheme).

Upon detecting that the attachment level is different from the level determined appropriate for the physiological measurement, in some embodiments, the apparatus may initiate a scheduling mechanism for the measurement. In some embodiments, the apparatus may comprise a switch that controls modes of operation of the sensor and/or devices connected to the apparatus. Based on the determination of attachment levels, the apparatus may activate or deactivate measurements being carried out (by the apparatus, additional sensors, etc.). In some embodiments, in addition to or instead of the ability to activate or deactivate measurements, the apparatus may have the capacity to alter the performance of the measurements according to the measured levels of attachment. For example, upon determining the attachment levels, the transceiver and/or the antennae may receive feedback to alter (e.g., increase or decrease) the radiation level if the apparatus determines the attachment to a surface has changed. In some instances, the apparatus may be monitoring the attachment level continuously or intermittently.

In some embodiments, attachment levels to a surface being different than their appropriate levels may mean excessive and/or long-lasting pressure is being applied to the surface of the body. For example, pressure sores or ulcers may develop if a body surface is exposed to a prolonged and/or excessive pressure, and the apparatus of the present disclosure may be used to monitor the pressure location and if needed provide alert as discussed above. In some embodiments, a compressible substance may be placed between the body surface and the apparatus, and RF signal reflections from the surface may be used in determining the level of the pressure (based on the attachment level, for example). In some embodiments, there may not be a compressible substance in between the surface and the apparatus, and reflections from layers below the surface may be used in determining attachment level and hence the pressure.

With reference to FIG. 1, in some embodiments, a picture of an example RF bistatic system (two antennas) for sensing attachment to a surface is shown. In some instances, one antenna, e.g., 101, operates as transmission antenna and the second one, e.g., 102, as receiving antenna. The antennae shown can be printed on printed circuit boards (PCBs), using a minimal form factor of bow-tie design, allowing wideband transmission and allowing for a wide range of dielectric constant material in the near field.

Figure 2:
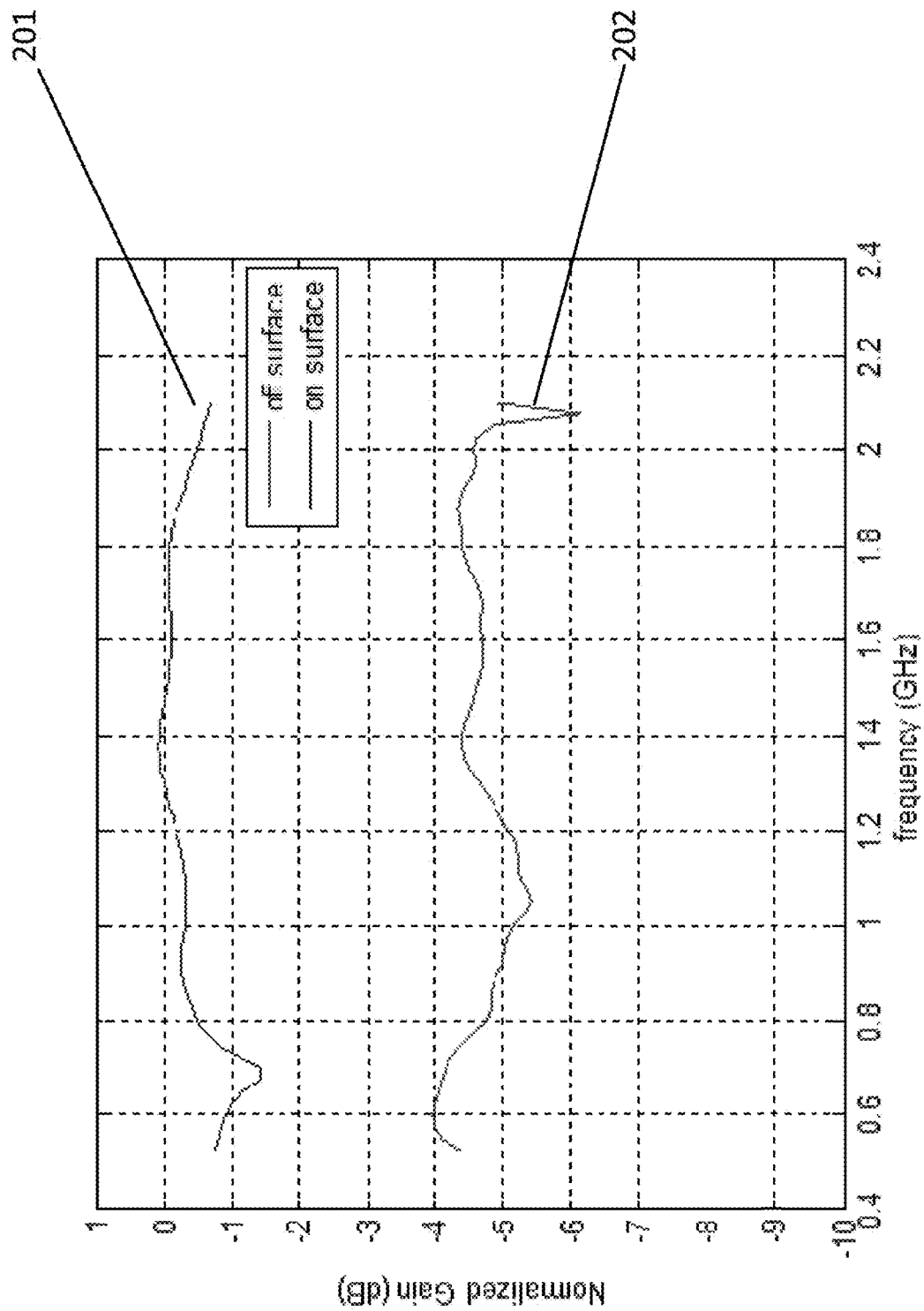
FIG. 2 illustrates an example normalized transmission loss (S21 parameter) comparison between embodiments when the antenna is attached to a surface, and when it is not.

With reference to FIG. 2, in some embodiments, an example transmission loss (S21 parameter) comparison between embodiments when the antenna is attached to a surface 201, and when it is not attached 202, is shown. It can be seen that S21 parameters are significantly different when comparing the two states (attached to the surface 201, and not attached 202). In the example shown, the antenna elements were first placed against human skin and then slightly shifted away from it. Consequently, overall transmission gain has dropped by 3-5 dB over the entire tested spectrum. The opposite result can also be achieved if, for example, an antenna designed to be matched to air is placed against a material different from air. In that case once the antenna is distanced from the material, transmission gain can increase significantly.

Figure 3:
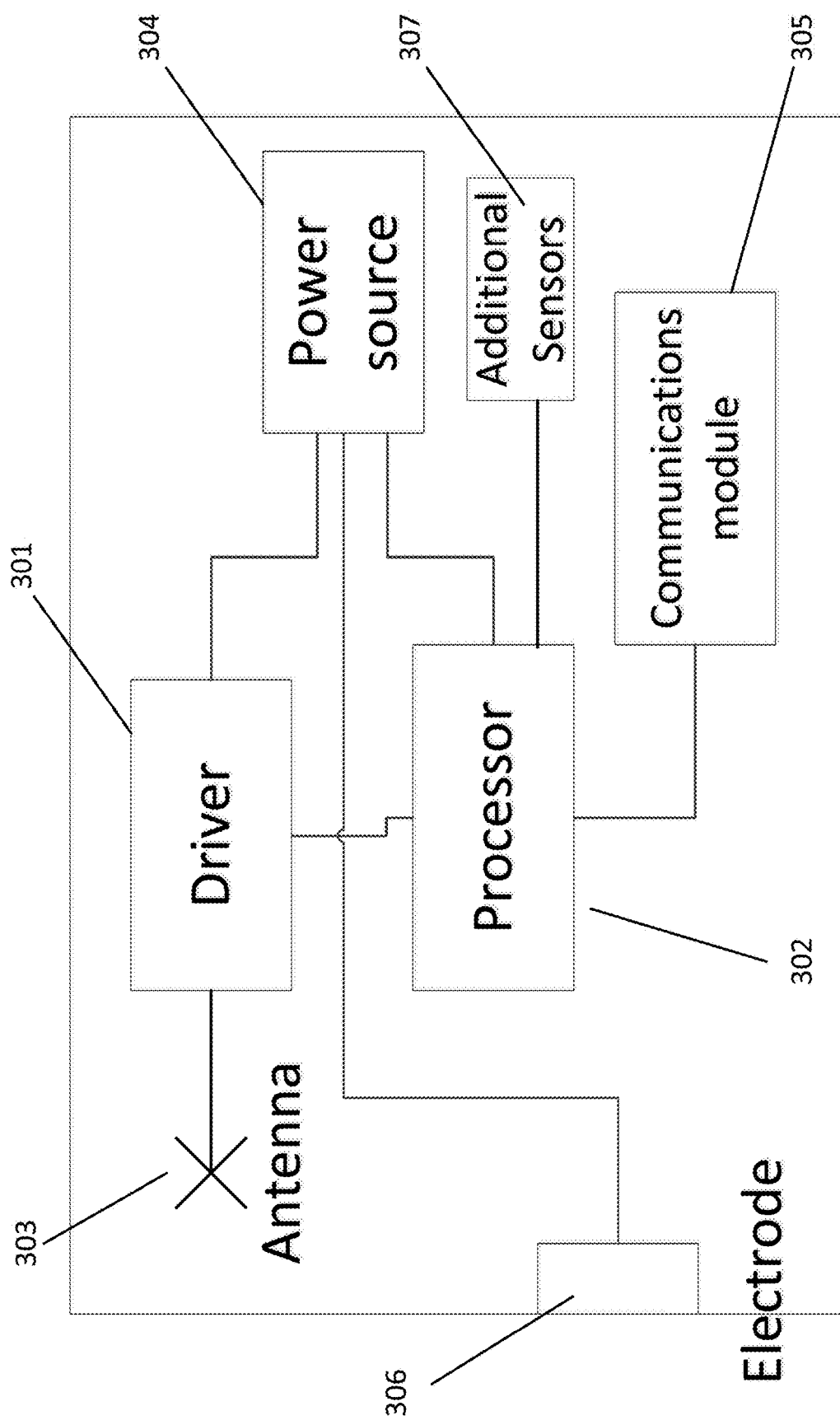
FIG. 3 shows a schematic block diagram comprising functional components of an apparatus for processing signals to determine attachment level of the apparatus to a surface.
Figure 4:
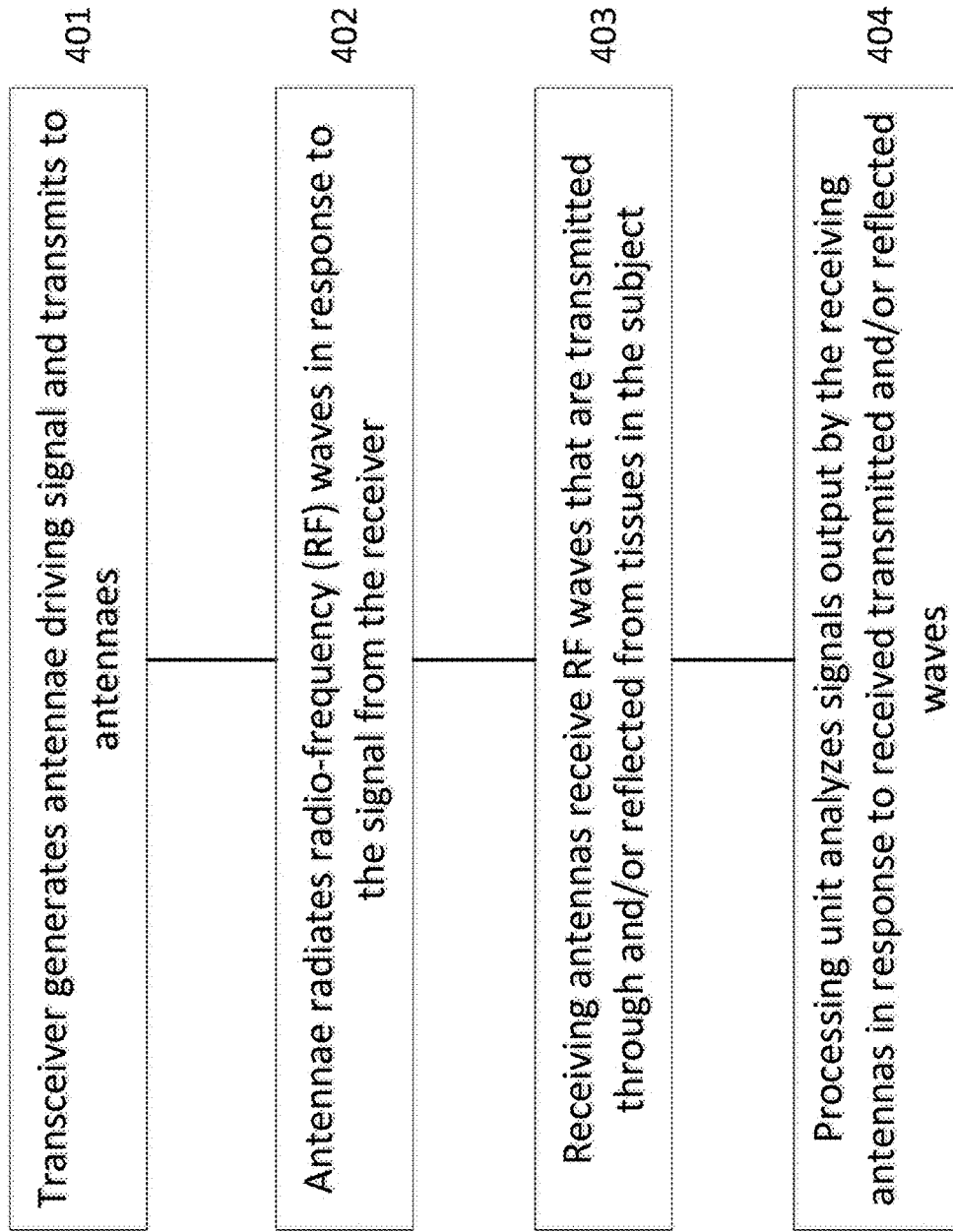
FIG. 4 is an example flow diagram illustrating the use of the disclosed apparatus for sensing changes in attachment of the apparatus to a surface of a human or animal body, according to an embodiment.

With reference to FIG. 3, in some embodiments, a schematic block diagram comprising functional components of an apparatus for processing signals to determine attachment level of the apparatus to a surface is shown. The apparatus comprises a processing circuitry including an antenna driver 301 and a processor 302. The antenna driver 301 drives one or more antennae 303 to emit RF waves onto the surface the apparatus is attached to. In some instances, the processor 302 processes signals that are output by the antennae 303 in response to waves reflected from the surface. The power source 304 supplies operating power to all the components of the apparatus, including to a communications module 305 used to relay data between the apparatus and an external device (e.g., computer). In some embodiments, electrodes 306 may be used to receive ECG signals from the body surface the apparatus is attached thereto. Further, additional sensors 307 such as accelerometers may be incorporated into the disclosed apparatus.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be an example and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure. Embodiments disclosed herein may also be combined with one or more features, as well as complete systems, devices and/or methods, to yield yet other embodiments and inventions. Moreover, some embodiments, may be distinguishable from the prior art by specifically lacking one and/or another feature disclosed in the particular prior art reference(s); i.e., claims to some embodiments may be distinguishable from the prior art by including one or more negative limitations.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An apparatus comprising:
a transceiver configured to generate and/or receive radio frequency (RF) electromagnetic signals;
one or more antennae configured for removable placement at a location on or immediately adjacent the skin of a human body and configured to:
radiate the generated RF electromagnetic signals towards an outer surface of the human body and through the skin of the human body,
output signals corresponding to received reflections of the RF electromagnetic signals; and
a processing circuitry configured to process the received reflections and/or the output signals so as to:
detect a nominal signal upon the apparatus being attached to a surface of the human body, the nominal signal corresponding to a nominal value,
determine values corresponding to one or more parameters of the received reflections and/or the output signals,
compare the determined values with the nominal value, and
based on the comparison, determining at least one of a state of attachment of the apparatus on the surface of the human body;
whether the apparatus is moving with respect to the surface of the human body, and
whether the apparatus is directly attached to the surface of the human body.

2. The apparatus of claim 1, wherein the nominal signal and at least one of the parameters comprise an amplitude of a respective reflected signal.

3. The apparatus of claim 2, wherein:
the nominal amplitude comprises a nominal amplitude set corresponding to a plurality of nominal amplitudes signals,
and
comparing comprises determining the sum of the absolute value of the difference of the amplitude of a reflected signal per frequency from the nominal amplitude set.

4. The apparatus of claim 1, wherein a waveform of the RF electromagnetic signals is continuous and/or based on step-frequency.

5. The apparatus of claim 1, wherein the RF electromagnetic signals range in frequency from about 300 MHz to about 300 GHz.

6. The apparatus of claim 1, wherein the one or more antennae comprise one or more of a monostatic antenna element, a bistatic antenna element, and a polystatic antenna element.

7. The apparatus of claim 1, wherein the one or more antennae comprise a flexible plane configured to conform to the outer surface, wherein the flexible plane includes a printed circuit board.

8. The apparatus of claim 1, further comprising an electrocardiogram (ECG) electrode configured to be attached to or contact the surface of the human body.

9. The apparatus of claim 8, wherein the ECG electrode produces ECG signals, and wherein the ECG signals are used to determine attachment level of the apparatus to the surface of the human body.

10. The apparatus of claim 1, further comprising therapy electrodes, and wherein the therapy electrodes are configured to provide electrical current to the human body.

11. The apparatus of claim 1, further comprising a wireless communication unit configured to wirelessly communicate with an external module.

12. The apparatus of claim 1, further comprising an alarm unit configured to provide a warning when the determination of the change in position of the apparatus with respect to the surface indicates attachment of the apparatus to the surface is below a predetermined attachment level threshold.

13. The apparatus of claim 12, further comprising an electrocardiogram (ECG) electrode configured to be attached to or contact the surface of the human body.

14. The apparatus of claim 13, further comprising therapy electrodes, and wherein the therapy electrodes are configured to provide electrical current to the human body.

15. The apparatus of claim 1, wherein the apparatus is connected to a device for measuring physiological parameters, and further comprising a switch unit configured to activate or deactivate the device based on the determination of the change in position of the apparatus with respect to the surface.

16. The apparatus of claim 1, wherein whether the apparatus is directly attached to the surface of the human body comprises at least one of whether the apparatus is in proximity to the surface within a known separation distance and whether the apparatus is incorporated into a wearable garment or adhesive patch.

17. A method for sensing attachment level of an apparatus with respect to a body surface to which the apparatus is attached to, comprising:
generating radio frequency (RF) electromagnetic signals;
radiating the generated RF electromagnetic signals towards an outer surfaced of the human body and through the skin of the human body via one or more antennae configured for removable placement at a location on or immediately adjacent the skin of a human or animal body;
outputting signals corresponding to received reflections of the RF electromagnetic signals;
processing the received reflections and/or the output signals so as to:
detect a nominal signal upon the apparatus being attached to a surface of the human body, the nominal signal corresponding to a nominal value,
determine values corresponding to one or more parameters of the received reflections and/or the output signals, and
compare the determined values with the nominal value, and
based on the comparison, determining at least one of:
a state of attachment of the apparatus on the surface of the human body;
whether the apparatus is moving with respect to the surface of the human body, and
whether the apparatus is directly attached to the surface of the human body.

18. The method of claim 17, wherein whether the apparatus is directly attached to the surface of the human body comprises at least one of whether the apparatus is in proximity to the surface within a known separation distance and whether the apparatus is incorporated into a wearable garment or adhesive patch.

* * * * *